United States Patent [19]

Gutman

[11] 4,279,638
[45] Jul. 21, 1981

[54] 3,5-DISUBSTITUTED 1,2,4-OXADIAZOLE HERBICIDAL ANTIDOTES

[75] Inventor: Arnold D. Gutman, Berkeley, Calif.

[73] Assignee: Stauffer Chemical Company, Westport, Conn.

[21] Appl. No.: 66,134

[22] Filed: Aug. 13, 1979

[51] Int. Cl.³ .................. A01N 43/82; A01N 37/16
[52] U.S. Cl. ............................................ 71/92; 71/72; 71/74; 71/76; 71/77; 71/88; 71/94; 71/95; 71/100
[58] Field of Search .................................. 71/92, 100

[56] References Cited

U.S. PATENT DOCUMENTS

| 2,913,327 | 11/1959 | Tilles et al. | 71/100 |
| 3,131,509 | 5/1964 | Hoffmann | 71/77 |
| 3,185,720 | 5/1965 | Tilles et al. | 260/455 A |
| 3,227,725 | 1/1966 | Eloy et al. | 424/263 |
| 3,770,754 | 11/1973 | Parsons | 71/92 |
| 3,947,263 | 3/1976 | Brouwer et al. | 71/92 |
| 4,124,372 | 11/1978 | Pallos et al. | 71/88 |
| 4,135,910 | 1/1979 | Howe | 71/92 |

*Primary Examiner*—Glennon H. Hollrah
*Attorney, Agent, or Firm*—Harry A. Pacini

[57] ABSTRACT

Compounds having the formula

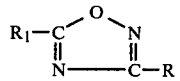

in which

R is selected from the group consisting of 1-4 carbon alkyl and 1-4 carbon haloalky; and $R_1$ is selected from the group consisting of 1-4 carbon haloalkyl and halo-substituted phenyl have utility as herbicidal antidotes.

23 Claims, No Drawings

3,5-DISUBSTITUTED 1,2,4-OXADIAZOLE HERBICIDAL ANTIDOTES

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate undesirable vegetation. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed pest. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre (lb/A) (0.0112 to 56 kilograms per hectare (k/ha)), usually from 0.1 to 25 lb/A (0.112 to 28 k/ha). The actual amount used depends upon several considerations including particular weed susceptibility and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. No. 4,021,224 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant, or antagonist. As used herein, "antidote" describes a compound which has the effect of establishing herbicidal selectivity.

Thiocarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently, the beneficent use of thiocarbamates requires the addition of an antidote.

3,5-disubstituted 1,2,4-oxadiazole compounds have previously been shown to have utility for treating root-knot nematodes, and as fungicides, systemic insecticides, and polymer plasticizers. See U.S. Pat. No. 3,227,725.

DESCRIPTION OF INVENTION

It has been discovered that the tolerances of several crops to thiocarbamate herbicides can be increased by the use of an antidotally effective amount of a 3,5-disubstituted 1,2,4-oxadiazole compound of the formula

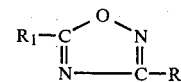

in which

R is selected from the group consisting of 1-4 carbon alkyl, preferably methyl, and 1-4 carbon haloalkyl, preferably mono- and trichloromethyl; and $R_1$ is selected from the group consisting of 1-4 carbon haloalkyl, preferably mono- and dichloromethyl, and halo-substituted phenyl.

This invention embodies a two-part herbicidal system comprised of (a) an antidotally effective amount of a compound of the formula

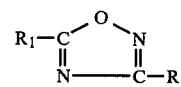

in which

R is selected from the group consisting of 1-4 carbon alkyl, preferably methyl, and 1-4 carbon haloalkyl, preferably mono- and trichloromethyl; and $R_1$ is selected from the group consisting of 1-4 carbon haloalkyl, preferably mono- and dichloromethyl, and halo-substituted phenyl; and (b) an herbicidally effective amount of a thiocarbamate of the formula

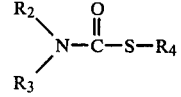

in which $R_2$ is selected from the group consisting of 1-6 carbon alkyl and 2-6 carbon alkenyl;

$R_3$ is selected from the group consisting of 1-6 carbon alkyl, 2-6 carbon alkenyl, cyclohexyl and phenyl; or $R_2$ and $R_3$ together form an alkylene ring; and $R_4$ is selected from the group consisting of 1-6 carbon alkyl, 1-4 carbon haloalkyl, 5-10 carbon alkylene ring, phenyl, substituted phenyl, wherein the substituents are 1-4 carbon alkyl, 1-4 carbon haloalkyl, and halo, benzyl, and substituted benzyl, wherein the substituents are 1-4 carbon alkyl, 1-4 carbon haloalkyl, and halo.

The terms "alkyl" and "alkenyl", as used herein, are intended to include both straight and branched-chain groups. "Haloalkyl" is meant to include mono-, di-, and tri-halo-substituted carbon. All carbon atom ranges are intended to be inclusive of both upper and lower limits.

The present invention also includes the method of selectively controlling undesirable vegetation in the presence of cultivated crops which comprises applying to a locus where control is desired (a) an antidotally effective amount of a compound of the formula

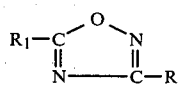

in which

R is selected from the group consisting of 1-4 carbon alkyl, preferably methyl, and 1-4 carbon haloalkyl, preferably mono- and trichloromethyl; and $R_1$ is selected from the group consisting of 1-4 carbon haloalkyl, preferably mono- and dichloromethyl, and halo-substituted phenyl; and (b) an herbicidally effective amount of a thiocarbamate of the formula

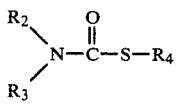

in which $R_2$ is selected from the group consisting of 1-6 carbon alkyl and 2-6 carbon alkenyl;

$R_3$ is selected from the group consisting of 1-6 carbon alkyl, 2-6 carbon alkenyl, cyclohexyl and phenyl; or $R_2$ and $R_3$ together form an alkylene ring; and $R_4$ is selected from the group consisting of 1-6 carbon alkyl, 1-4 carbon haloalkyl, 5-10 carbon alkylene ring, phenyl, substituted phenyl, wherein the substituents are 1-4 carbon alkyl, 1-4 carbon haloalkyl, and halo, benzyl, and substituted benzyl, wherein the substituents are 1-4 carbon alkyl, 1-4 carbon haloalkyl, and halo.

The thiocarbamate herbicides are generally incorporated into the soil prior to planting. The antidote compound may be combined with the herbicide as a tank mix as it is incorporated into the soil. This is referred to as the "Pre-plant Incorporation" (PPI) Method of Application. The antidote may also be applied by the "In-furrow" (IF) Method of Application which consists of spraying the seeds and the herbicidally treated soil with the antidote compound prior to covering the seeds with soil.

TESTING OF THE INVENTION

The thiocarbamates of the present compositions can be prepared by the procedures described in the commonly assigned and expired U.S. Pat. Nos. 2,913,327 and 3,185,720.

The 3,5-disubstituted 1,2,4-oxadiazoles of the compositions of this invention can be prepared by the procedures described in U.S. Pat. No. 3,227,725.

Table I contains representative 3,5-disubstituted 1,2,4-oxadiazole antidote compounds which were tested as part of the herbicidal compositions of this invention.

TABLE I 3,5-DISUBSTITUTED 1,2,4-OXADIAZOLE HERBICIDAL ANTIDOTES

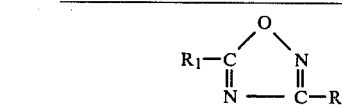

| Compound Number | R | $R_1$ | Chemical Name | Physical Constant |
|---|---|---|---|---|
| 1 | $CH_3$ | $CHCl_2$ | 3-methyl-5-dichloromethyl-1,2,4-oxadiazole | $n_D^{30}$ 1.4533 |
| 2 | $CH_2Cl$ | $CH_2Cl$ | 3,5-di-chloromethyl-1,2,4-oxadiazole | $n_D^{30}$ 1.4713 |
| 3 | $CH_2Cl$ | $CHCl_2$ | 3-chloromethyl-5-dichloromethyl-1,2,4-oxadiazole | $n_D^{30}$ 1.4824 |
| 4 | $Cl_3C$ | $CH_2Cl$ | 3-trichloromethyl-5-chloromethyl-1,2,4-oxadiazole | $n_D^{30}$ 1.4860 |
| 5 | $Cl_3C$ | $CHCl_2$ | 3-trichloromethyl-5-dichloromethyl-1,2,4-oxadiazole | $n_D^{30}$ 1.4860 |
| 6 | $Cl_3C$ | 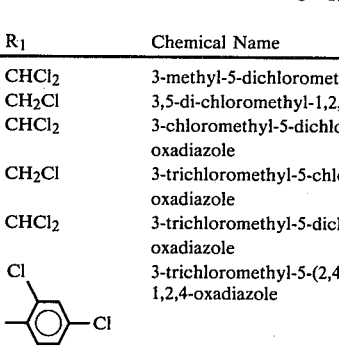 | 3-trichloromethyl-5-(2,4-dichlorophenyl)-1,2,4-oxadiazole | m.p. 100–102° C. |

Stock solutions of the various thiocarbamate herbicides were prepared by dissolving the requisite amount of the herbicide in water.

Stock solutions of each antidote compound were prepared by dissolving the requisite amount in acetone. The herbicide and antidote compositions and their equivalent rates of application appear in Tables II and III.

TABLE II

| Herbicidal Stock Solutions | | | |
|---|---|---|---|
| Composition | | Application | |
| Herbicide (mg) | Water (ml) | ml soln | ~ lb/A |
| S-propyl-N,N-dipropyl-thiocarbamate | | | |
| 250 | 250 | 5 | 1.00 |
| 449 | 400 | 5 | 1.25 |
| 1798 | 400 | 5 | 5.00 |
| 3000 | 500 | 5 | 6.00 |
| S-ethyl-N-ethyl-N-cyclohexylthiocarbamate | | | |
| 780 | 250 | 5 | 3.00 |
| S-ethyl-N,N-dipropyl thiocarbamate | | | |
| 2240 | 350 | 5 | 6.00 |

TABLE III

Antidote Stock Solutions
Antidote: 3,5-Disubstituted 1,2,4-Oxadiazole

| Composition | | Application | | |
|---|---|---|---|---|
| Antidote (mg) | Acetone (ml) | ml soln | lb/A | Method |
| 95 | 15 | 0.3 | 1.00 | IF |
| 95 | 15 | 1.5 | 5.00 | IF |
| 100 | 25 | 1.0 | 1.00 | PPI |
| 24 | 15 | 5.0 | 2.00 | PPI |
| Stock Solution A: | | | | |
| 60 | 15 | 5.0 | 5.00 | PPI |
| Dilutions | | | | |
| Stock Solution B: | | | | |
| 5 ml of A | 45 | 5.0 | 0.50 | PPI |
| Stock Solution C: | | | | |
| 5 ml of B | 45 | 5.00 | 0.05 | PPI |

All of the soil used in the tests described herein was loamy sand soil treated with 50 parts per million (ppm) each of a commercially available fungicide, cis-N[(trichloromethyl)thio]-4-cyclohexane-1,2-dicarboximide, and an 18-18-18 fertilizer which contains 18% by weight equivalent each of nitrogen, phosphorus pentoxide, and potassium oxide.

For the pre-plant incorporation (PPI) method, the herbicide and the antidote of each test group were incorporated into the treated soil as a tank mix using a five gallon rotary mixer. Control flats used for injury rating comparisons contained only the herbicide treated soil.

For in-furrow (IF) antidote applications, planting flats were filled with the soil treated by PPI of the herbicide. A one pint sample of soil removed from each flat was retained to cover the seeds after treatment. After leveling and furrowing the soil, seeds of the crop or weed species were planted ½ inch deep. Each flat was divided in half by a wooden barrier. A stock solution of the antidote was atomized directly onto the exposed seeds and soil in the open furrows of one-half of the flat. The seeds were then covered with the previously removed soil. The untreated sections of the flats containing identical herbicide concentrations were compared for observed differences which would indicate lateral movement of the antidote through the soil.

The flats were placed on greenhouse benches where temperature was maintained between 70° and 90° F. (21.11° to 32.22° C.). The soil was watered by sprinkling as needed to assure good plant growth.

Control flats contained crops treated with herbicides only at the various rates and methods of application.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were milo, wheat, cotton, rice, barley, corn, and soybeans. Those compounds which showed substantial crop injury reduction were further tested at reduced rates. The herbicides and antidote compositions were then screened on at least two weed species. The weed species tested for control included watergrass (*Echinochloa crusgalli*), foxtail (*Setaria viridis*, Johnsongrass (*Sorghum halepense*), and shattercane (*Sorghum bicolor*).

KEY TO TABLES IV AND V

Compound numbers in these tables correspond to antidote compound numbers and their chemical description in Table I. Compound No. 6 omitted in Table V was not tested on weed species.

| | | |
|---|---|---|
| Application: | IF | - In-furrow surface |
| | PPI | - Pre-plant incorporation of herbicide and antidote as a tank mix |
| | | Herbicides |
| VERNAM® | | S-propyl N,N-dipropylthiocarbamate. |
| EPTAM® | | S-ethyl N,N-dipropylthiocarbamate. Vernam and Eptam are described in U.S. Pat. No. 2,913,327 |
| RO-NEET® | | S-ethyl N-ethyl-N-cyclohexylthiocarbamate, as described in U.S. Pat. No. 3,185,720. |
| Rates: | | All rates are shown in pounds per acre. |
| Injury Ratings: | | |
| | U = | Antidotally untreated; % injury 4 weeks after herbicide application. |
| | T = | Antidotally treated; % injury 4 weeks after treatment with herbicide plus antidote compound. |
| | — = | Indicates no change. |

TABLE IV

Antidotal Effectiveness
% Crop Injury

| Cmpd. No. | Antidote Rate | Method | Herbicide Name | Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
| 1 | 5.00 | IF | VERNAM | 1.25 | 90 | 40 | 100 | — | 70 | — | 100 | — | 75 | 65 | | | | |
| | 5.00 | IF | VERNAM | 6.00 | | | | | | | | | | | 90 | 20 | 40 | — |
| | 1.00 | IF | RO-NEET | 3.00 | 85 | 65 | | | | | | | | | | | | |
| | 5.00 | IF | RO-NEET | 3.00 | 85 | 30 | | | | | | | | | | | | |
| | 1.00 | PPI | RO-NEET | 3.00 | 80 | 10 | | | | | | | | | | | | |
| | 5.00 | PPI | RO-NEET | 3.00 | 80 | 10 | | | | | | | | | | | | |
| | 1.00 | PPI | RO-NEET | 3.00 | 90 | 80 | | | | | | | | | | | | |
| | 2.00 | PPI | RO-NEET | 3.00 | 90 | 75 | | | | | | | | | | | | |
| | 5.00 | PPI | RO-NEET | 3.00 | 90 | 75 | | | | | | | | | | | | |
| | 0.05 | PPI | EPTAM | 6.00 | | | | | | | | | | | 80 | — | | |
| | 0.50 | PPI | EPTAM | 6.00 | | | | | | | | | | | 80 | 0 | | |
| | 5.00 | PPI | EPTAM | 6.00 | | | | | | | | | | | 80 | 0 | | |
| 2 | 5.00 | IF | VERNAM | 1.25 | 100 | — | 90 | 100 | 60 | 70 | 95 | 100 | 85 | 70 | | | | |
| | 5.00 | IF | VERNAM | 6.00 | | | | | | | | | | | 90 | 0 | 65 | 100 |
| | 0.50 | PPI | VERNAM | 6.00 | | | | | | | | | | | | | 60 | — |
| | 2.00 | PPI | VERNAM | 6.00 | | | | | | | | | | | | | 60 | 50 |
| | 0.50 | PPI | VERNAM | 6.00 | | | | | | | | | | | | | 55 | — |
| | 2.00 | PPI | VERNAM | 6.00 | | | | | | | | | | | | | 55 | — |
| | 0.05 | PPI | EPTAM | 6.00 | | | | | | | | | | | 85 | 45 | | |
| | 0.50 | PPI | EPTAM | 6.00 | | | | | | | | | | | 85 | 35 | | |
| | 5.00 | PPI | EPTAM | 6.00 | | | | | | | | | | | 85 | 0 | | |

TABLE IV-continued

Antidotal Effectiveness
% Crop Injury

| Antidote | | | Herbicide | | Milo | | Wheat | | Cotton | | Rice | | Barley | | Corn | | Soybean | |
|---|---|---|---|---|---|---|---|---|---|---|---|---|---|---|---|---|---|---|
| Cmpd. No. | Rate | Method | Name | Rate | U | T | U | T | U | T | U | T | U | T | U | T | U | T |
| 3 | 5.00 | IF | VERNAM | 1.25 | 100 | 40 | 85 | 60 | 60 | — | 100 | 20 | 80 | 60 | | | | |
| | 5.00 | IF | VERNAM | 6.00 | | | | | | | | | | | 90 | 0 | 60 | 100 |
| | 1.00 | PPI | VERNAM | 1.00 | | | | | | | 90 | 40 | | | | | | |
| | 5.00 | PPI | VERNAM | 1.00 | | | | | | | 90 | — | | | | | | |
| | 1.00 | PPI | VERNAM | 5.00 | | | | | | | | | | | | | 60 | 40 |
| | 5.00 | PPI | VERNAM | 5.00 | | | | | | | | | | | | | 60 | — |
| | 0.50 | PPI | VERNAM | 6.00 | | | | | | | | | | | | | 70 | 60 |
| | 2.00 | PPI | VERNAM | 6.00 | | | | | | | | | | | | | 55 | — |
| | 1.00 | IF | VERNAM | 6.00 | | | | | | | | | | | | | 50 | — |
| | 1.00 | IF | RO-NEET | 3.00 | 75 | 30 | | | | | | | | | | | | |
| | 5.00 | IF | RO-NEET | 3.00 | 75 | 10 | | | | | | | | | | | | |
| | 0.50 | PPI | EPTAM | 6.00 | | | | | | | | | | | 70 | — | | |
| | 5.00 | PPI | EPTAM | 6.00 | | | | | | | | | | | 70 | 0 | | |
| 4 | 5.00 | IF | VERNAM | 1.25 | 90 | — | 100 | — | 70 | — | 100 | 15 | 75 | — | | | | |
| | 5.00 | IF | VERNAM | 6.00 | | | | | | | | | | | 90 | — | 40 | — |
| | 1.00 | PPI | VERNAM | 1.00 | | | | | | | 90 | 85 | | | | | | |
| | 5.00 | PPI | VERNAM | 1.00 | | | | | | | 90 | 60 | | | | | | |
| 5 | 5.00 | IF | VERNAM | 1.25 | 90 | 70 | 100 | 85 | 70 | — | 100 | 40 | 75 | — | | | | |
| | 5.00 | IF | VERNAM | 6.00 | | | | | | | | | | | 90 | 60 | 40 | — |
| | 1.00 | IF | VERNAM | 1.00 | | | | | | | 95 | 35 | | | | | | |
| | 5.00 | IF | VERNAM | 1.00 | | | | | | | 95 | 45 | | | | | | |
| | 1.00 | PPI | VERNAM | 1.00 | | | | | | | 95 | 50 | | | | | | |
| | 2.00 | PPI | VERNAM | 1.00 | | | | | | | 95 | 80 | | | | | | |
| | 5.00 | PPI | VERNAM | 1.00 | | | | | | | 95 | 65 | | | | | | |
| 6 | 5.00 | IF | VERNAM | 1.25 | 90 | 60 | 100 | — | 70 | 90 | 100 | 65 | 75 | 55 | | | | |
| | 5.00 | IF | VERNAM | 6.00 | | | | | | | | | | | 90 | — | 40 | — |

TABLE V

Herbicidal Effectiveness
% Weed Injury

| Antidote | | | Herbicide | | Watergrass | | Foxtail | | Johnsongrass | | Shattercane | |
|---|---|---|---|---|---|---|---|---|---|---|---|---|
| Cmpd. No. | Rate | Method | Name | Rate | U | R | U | T | U | T | U | T |
| 1 | 1.00 | IF | RO-NEET | 3.00 | 90 | — | 90 | — | | | | |
| | 5.00 | IF | RO-NEET 3.00 | 90 | — | 90 | — | | | | | |
| | 1.00 | PPI | RO-NEET | 3.00 | 90 | — | 90 | — | | | | |
| | 5.00 | PPI | RO-NEET | 3.00 | 90 | — | 90 | — | | | | |
| | 1.00 | PPI | RO-NEET | 3.00 | | | 90 | — | | | 95 | — |
| | 2.00 | PPI | RO-NEET | 3.00 | | | 90 | — | | | 95 | — |
| | 5.00 | PPI | RO-NEET | 3.00 | | | 90 | — | | | 95 | — |
| | 0.05 | PPI | EPTAM | 6.00 | 95 | — | 100 | — | | | | |
| | 0.50 | PPI | EPTAM | 6.00 | 95 | — | 100 | — | | | | |
| | 5.00 | PPI | EPTAM | 6.00 | 95 | — | 100 | — | | | | |
| 2 | 0.50 | PPI | VERNAM | 6.00 | 99 | — | 99 | — | | | | |
| | 2.00 | PPI | VERNAM | 6.00 | 99 | — | 99 | — | | | | |
| | 0.50 | PPI | VERNAM | 6.00 | 98 | — | 100 | — | | | | |
| | 2.00 | PPI | VERNAM | 6.00 | 98 | — | 100 | — | | | | |
| | 0.05 | PPI | EPTAM | 6.00 | 98 | — | | | 98 | — | | |
| | 0.50 | PPI | EPTAM | 6.00 | 98 | — | | | 98 | — | | |
| | 5.00 | PPI | EPTAM | 6.00 | 98 | 80 | | | 98 | 70 | | |
| 3 | 1.00 | PPI | VERNAM | 1.00 | 100 | — | 85 | — | | | | |
| | 5.00 | PPI | VERNAM | 1.00 | 100 | — | 85 | — | | | | |
| | 1.00 | PPI | VERNAM | 5.00 | 95 | — | 95 | — | | | | |
| | 5.00 | PPI | VERNAM | 5.00 | 95 | — | 95 | — | | | | |
| | 0.50 | PPI | VERNAM | 6.00 | 98 | — | 98 | — | | | | |
| | 2.00 | PPI | VERNAM | 6.00 | 99 | — | 98 | — | | | | |
| | 1.00 | IF | VERNAM | 6.00 | 98 | — | 95 | — | | | | |
| | 1.00 | IF | RO-NEET | 3.00 | | | 80 | — | | | 95 | — |
| | 5.00 | IF | RO-NEET | 3.00 | | | 80 | — | | | 95 | — |
| | 0.50 | PPI | EPTAM | 6.00 | 100 | — | 100 | — | | | | |
| | 5.00 | PPI | EPTAM | 6.00 | 100 | — | 100 | — | | | | |
| 4 | 1.00 | PPI | VERNAM | 1.00 | 100 | — | 85 | — | | | | |
| | 5.00 | PPI | VERNAM | 1.00 | 100 | — | 85 | — | | | | |
| 5 | 1.00 | IF | VERNAM | 1.00 | 95 | — | 85 | — | | | | |
| | 5.00 | IF | VERNAM | 1.00 | 95 | — | 85 | — | | | | |
| | 1.00 | PPI | VERNAM | 1.00 | 95 | — | 80 | — | | | | |
| | 2.00 | PPI | VERNAM | 1.00 | 95 | — | 80 | — | | | | |
| | 5.00 | PPI | VERNAM | 1.00 | 95 | — | 80 | — | | | | |

FORMULATIONS

The object of the formulation is to apply the compositions to the locus where control is desired by a convenient method. The "locus" may include soil, seeds, seedlings, and vegetation.

The amount of antidote compound which comprises part of a herbicidal composition will generally range from approximately 0.001 to 30 parts by weight per weight of the herbicidal compound.

Formulations will generally contain several additives. Among these are some inert ingredients and diluent carriers such as organic solvents, water, oil and water, water in oil emulsions, carriers of dusts and granules, and surface active wetting, dispersing, and emulsifying agents.

Fertilizers, e.g., ammonium nitrate, urea and superphosphate, may also be included.

Aids to rooting and growth, e.g., compost, manure, humus, sand, etc., may likewise be included.

The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79-84.

Granules comprise the herbicidal composition impregnated on a particulate inert carrier having a particle size of about 1 to 2 millimeters (mm) in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

I claim:

1. A composition consisting essentially of
(a) an antidotally effective amount of a compound of the formula $$\begin{array}{c} R_1-C\overset{O}{\underset{\|}{\phantom{-}}}N \\ \| \quad \| \\ N\text{------}C-R \end{array}$$

in which
R is selected from the group consisting of 1-4 carbon alkyl and 1-4 carbon haloalkyl;
$R_1$ is selected from the group consisting of 1-4 carbon haloalkyl and halo-substituted phenyl; and
(b) an herbicidally effective amount of a thiocarbamate of the formula $$\begin{array}{c} R_2 \quad\quad O \\ \diagdown \quad\quad \| \\ N-C-S-R_4 \\ \diagup \\ R_3 \end{array}$$

in which
$R_2$ is selected from the group consisting of 1-6 carbon alkyl;
$R_3$ is selected from the group consisting of 1-6 carbon alkyl, and cyclohexyl and
$R_4$ is selected from the group consisting of 1-6 carbon alkyl.

2. A composition according to claim 1 in which $R_2$, $R_3$ and $R_4$ are each propyl.

3. A composition according to claim 2 in which R is methyl and $R_1$ is dichloromethyl.

4. A composition according to claim 2 in which R and $R_1$ are each halomethyl.

5. A composition according to claim 4 in which R and $R_1$ are each chloromethyl.

6. A composition according to claim 4 in which R is chloromethyl and $R_1$ is dichloromethyl.

7. A composition according to claim 4 in which R is trichloromethyl and $R_1$ is chloromethyl.

8. A composition according to claim 4 in which R is trichloromethyl and $R_1$ is dichloromethyl.

9. A composition according to claim 1 in which $R_2$ is ethyl, $R_3$ is cyclohexyl and $R_4$ is ethyl.

10. A composition according to claim 9 in which R is methyl and $R_1$ is dichloromethyl.

11. A composition according to claim 9 in which R is chloromethyl and $R_1$ is dichloromethyl.

12. A composition according to claim 1 in which $R_2$ and $R_3$ are each propyl and $R_4$ is ethyl.

13. A composition according to claim 12 in which R is methyl and $R_1$ is dichloromethyl.

14. A composition according to claim 12 in which R and $R_1$ are each halomethyl.

15. A composition according to claim 14 in which R and $R_1$ are each chloromethyl.

16. A composition according to claim 14 in which R is chloromethyl and $R_1$ is dichloromethyl.

17. A method of controlling undesirable vegetation and reducing herbicidal crop injury due to a thiolcarbamate herbicide which comprises applying to the locus where control is desired a non-phytotoxic antidotally effective amount of a compound of the formula

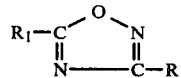

in which

R is selected from the group consisting of 1-4 carbon alkyl and 1-4 carbon haloalkyl;

$R_1$ is selected from the group consisting of 1-4 carbon haloalkyl and halo-substituted phenyl and an herbicidally effective amount of a thiolcarbamate of the formula

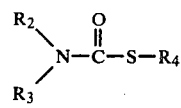

in which $R_2$ is selected from the group consisting of 1-6 carbon alkyl;

$R_3$ is selected from the group consisting of 1-6 carbon alkyl, and cyclohexyl and $R_4$ is selected from the group consisting of 1-6 carbon alkyl.

18. A method according to claim 17 in which R is methyl and $R_1$ is dichloromethyl.

19. A method according to claim 17 in which R and $R_1$ are each halomethyl.

20. A method according to claim 19 in which R and $R_1$ are each chloromethyl.

21. A method according to claim 19 in which R is chloromethyl and $R_1$ is dichloromethyl.

22. A method according to claim 19 in which R is trichloromethyl and $R_1$ is chloromethyl.

23. A method according to claim 19 in which R is trichloromethyl and $R_1$ is dichloromethyl.

* * * * *